May 7, 1940. M. H. HORVATH Plant Pat. 387
ROSE
Filed Dec. 13, 1939
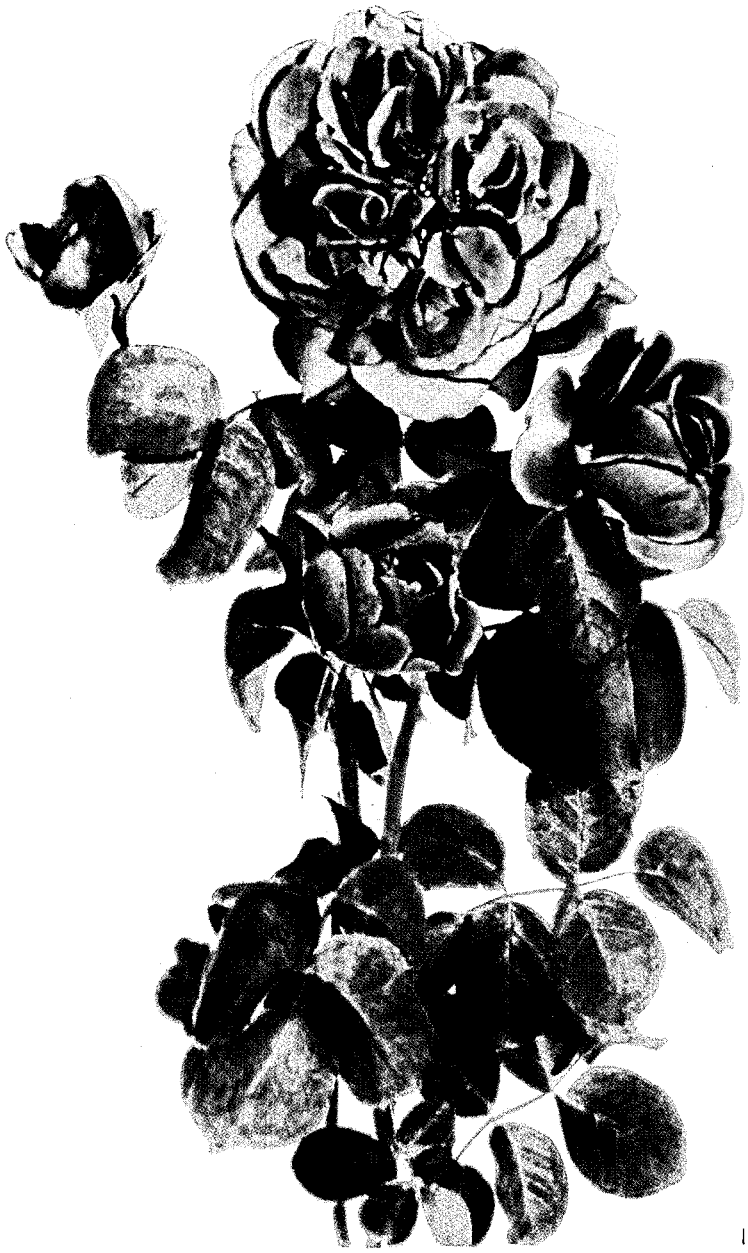
INVENTOR
MICHAEL H. HORVATH
BY John H. Ravenscroft,
HIS ATTORNEY Patented May 7, 1940

Plant Pat. 387

UNITED STATES PATENT OFFICE

387

ROSE

Michael H. Horvath, Mentor, Ohio

Application December 13, 1939, Serial No. 309,067

1 Claim. (Cl. 47—61)

This invention relates to a new variety of rose, a *Rosa setigera* hybrid.

The variety was originally produced by crossing a variety Alpha, as the female or seed parent, with a variety President Coolidge, as the male or pollen parent. President Coolidge, in turn, is a hybrid produced by Michael H. Horvath, as a result of a cross between Chateau de Clos Vougeot, a hybrid perpetual, as the male or pollen parent and the variety Alpha, as the female or seed parent. Alpha, in turn, is the result of a cross between *Rosa setigera,* as the female or seed parent, and *Rosa sempervirens* as the pollen or male parent, and produced by Michael H. Horvath. The variety has been asexually reproduced true to form in considerable quantity.

The variety is exceptionally hardy and above average in resistance to disease. It has been grown unprotected in the northeastern, middle Atlantic and midwestern regions of the United States and west to Iowa, and appears to be adapted for growth, unprotected, generally in the United States and elsewhere throughout regions in the temperate zones. It can be grown, protected, in colder regions.

The plant is a vigorous climber with plentiful canes and attains a height of eight to twelve feet.

The leaves are abundant, closely set and semi-glabrous and, on the upper surfaces, are green comparable to Maerz & Paul Plate No. 23–A–10. They are very resistant to mildew and black-spot and of exceptional lasting qualities, being sound until the end of the growing season.

The flowers are abundant, very large, semi-globular, and perfectly formed. They are borne on generally upright, stiff spur branches, twelve to eighteen inches long with upright and strong pedicels which support the flowers without bending. They occur singly and in groups of three, the buds forming a group, and usually opening one at a time. The flowers are distributed over the plant, beginning one or two feet from the ground or base. In color, the flowers are intense and brilliant salvia comparable to Maerz & Paul Plate No. 3–L–6, with a center of small clusters of stamens with yellow pollen. An unusual characteristic is that, after the flowers are full blown, their color does not fade but, on the contrary, intensifies throughout the blooming period.

Each flower has from fifty-five to sixty petals which are imbricated and, near the center of the flower, are deeply curved and concave generally toward the center of the flower for their full length and tend toward an upright position. The outer petals slope more gradually outwardly and upwardly and are less concave, being semi-globular for the major portion of their extent and having substantial smoothly recurving or reflex margins. The petals are slightly lighter and less intense in color near their bases.

The variety is a vigorous climber and a good bloomer, bearing uniformly throughout a blooming season of four to five weeks, the flowers having good lasting qualities cut or uncut, with the peculiar characteristic of intensification of color continuously as the flowers age and until the petals drop, which feature is one feature particularly distinguishing it from other varieties now known. It is distinguished further in the perfect form of the flowers, the lasting qualities of the foliage and its hardiness and resistance to disease.

The drawing further illustrates the characteristics of the variety which are not present in the parent stocks and which enhance its beauty and desirability.

The following tabulation is a detailed description of the new variety:

*General*

Parentage:
- *Seedling—seed parent.*—Alpha.
- *Pollen parent.*—President Coolidge.

Classification:
- *Botanic.*—*Setigera* hydrid.

*Flower*

Blooming habit:
- Location where observations were made.—Trial field of Michael H. Horvath, Mentor, Ohio.
- *Flowering.*—Recurrent, June and August.

Bud:
- *Size.*—Large.
- *Form.*—Semi-globular.
- *Color.*—When sepals first divide—red, comparable to Maerz & Paul Plate No. 3–L–6. When petals begin to unfurl—red, comparable to Maerz & Paul Plate No. 3–L–6. When half blown—red, comparable to Maerz & Paul Plate No. 3–L–6.
- *Sepals.*—Regular and large, long pointed, curled back, and light green.
- *Calyx.*—Shape—regular. Size—medium. Aspect—smooth and uniform. Odor when rubbed—slight rose fragrance.
- *Peduncle.*—Length—two and one-half to three inches. Aspect—very smooth, very small prickles almost amounting to pubescence. Color—green. Strength—medium but ample to hold flowers upright. Opening—regular and not much affected by weather conditions.

Bloom:
- *Size.*—Three and one-half to four inches.
- *Borne.*—Singly and in threes.
- *Stems.*—Upright and strong.
- *Form.*—When first opened—semi-globular.
- *Permanence.*—Good and flowers uniformly distributed through blooming periods.

Petalage: Number of petals under normal conditions—fifty-five to sixty.

*Color.*—Center of flower—intense salvia, comparable to Maerz & Paul Plate No. 3–L–6. Outer petals—same. Base of petals—slightly lighter and less intense. Inside of petals—same as outer petals. Reverse of petals—slightly lighter than outer petals. General tonality from a distance—intense salvia.

*Variegations.*—Increases in intensity and quality continuously throughout the entire blooming period.

*Discoloration.*—General tonality at end of first and second days—none. Third day—color intensifies.

Petals:

*Texture.*—Heavy.

*Appearance.*—Inside—intense salvia, outside—same.

*Form.*—Semi-globular with medium smoothly recurving margins.

*Arrangement.*—Imbricated to center.

*Petaloids in center.*—None.

*Persistance.*—Good, cut or uncut, until shed.

*Fragrance.*—Rose.

*Nature.*—Medium.

*Lasting quality.*—On plant—good. As a cut flower—good.

Genital organs:

*Stamens.*—Normal size.

*Color.*—Yellow.

*Arrangement.*—Regular.

*Stamens, filaments (threads).*—Regular and medium length.

*Color.*—Light cream.

*Pollen.*—Yellow.

*Styles.*—Bottle green, medium size and normal.

*Stigmas.*—Average size and creamy white.

*Ovaries.*—Sparse.

Fruit:

*Variety.*—Small.

*Form.*—Pear shaped.

*Aspect.*—Smooth.

*Color at maturity.*—Yellow slightly speckled with red.

*Sepals.*—Normal.

*Plant*

Form: A climber.

Growth: Vigorous and from eight to twelve feet.

Foliage: Closely set, semi-glabrous.

*Size.*—Medium.

*Quantity.*—Abundant.

*Color.*—New foliage: Upper side—green, comparable to Maerz & Paul Plate 23–A–10; under side—light green. Old foliage: upper side—green; under side—lighter green.

*Shape.*—Regular to obovate with short points.

*Texture.*—Upper side—heavy and coriaceous, under side—normal. Ribs and veins—distinct.

*Edge.*—Serrated, serrations—regular.

*Rachis.*—Medium or short, smooth with prickles or thorns evenly distributed. Color—green. Under side—lighter green.

*Stipules.*—Smooth and semi-spherical.

*Disease resistance.*—Good and resistant to mildew and black-spot.

Wood:

*New wood.*—Color—green, comparable to Maerz & Paul Plate No. 23–E–10. bark—green and smooth.

*Old wood.*—Color—green, as per new wood. Bark—green with brown streaks.

Thorns:

*Quantity.*—On main stalks from base—moderate. On laterals from stalk—moderate.

*Form.*—Moderately wide base and downward slope.

*Color.*—Greyish brown.

*Position.*—Unevenly distributed on main stalks and laterals.

*Prickles.*—None.

*Short needles.*—None.

Having now fully shown and described my new variety of rose and the mode of its production, what I claim and desire to secure by Letters Patent of the United States is:

A variety of hybrid rose as herein shown and described, and characterized particularly by very large flowers of great beauty in shape and color, with petals of brilliant and intense salvia and of which the color increases in intensity throughout the blooming period, the lasting qualities of the foliage which is sound to the end of the season and very resistant to black-spot, mildew and diseases generally.

MICHAEL H. HORVATH.